United States Patent [19]
Smith et al.

[11] Patent Number: 6,045,992
[45] Date of Patent: Apr. 4, 2000

[54] REVERSE TRANSCRIPTASE DETECTION AND INHIBITION

[75] Inventors: Steven S. Smith, Los Angeles; Bruce E. Kaplan, Claremont, both of Calif.

[73] Assignee: City of Hope, Duarte, Calif.

[21] Appl. No.: 08/107,579

[22] Filed: Aug. 18, 1993

Related U.S. Application Data

[60] Division of application No. 07/745,922, Aug. 16, 1991, Pat. No. 5,708,154, which is a continuation-in-part of application No. 07/598,665, Oct. 23, 1990, which is a continuation-in-part of application No. 07/317,670, Mar. 1, 1989, abandoned, which is a continuation-in-part of application No. 07/314,935, Feb. 24, 1989, abandoned.

[51] Int. Cl.⁷ .............................. C12Q 1/70; C12Q 1/68
[52] U.S. Cl. ...................................... 435/5; 435/6
[58] Field of Search .................... 435/6, 7.4, 7.5, 435/7.72, 5; 536/22.1

[56] References Cited

U.S. PATENT DOCUMENTS

| 4,683,195 | 7/1987 | Mullis et al. ............................ 435/6 |
| 5,215,899 | 6/1993 | Dattagupta ............................... 435/6 |

OTHER PUBLICATIONS

Urdea et al. Nucl. Acid. Res 16: 4937–4956 (1988) "A Comparison of non–radioisotopic hybridization . . . ".
Somogyi et al, J. Virol. Meth. 27:269–276 (1990) "A Solid phase reverse transcriptase . . . ".
Gene 44:263–270 (1986) Kalisch et al.
Molecular Cloning, Sambrook et al, (1982) p. 128.

*Primary Examiner*—Eggerton A. Campbell
*Attorney, Agent, or Firm*—Rothwell, Figg, Ernst & Kurz

[57] ABSTRACT

A reverse transcriptase assay is described. A modular nanostructure comprising relatively small and relatively long RNA sequences is utilized in the assay.

2 Claims, 1 Drawing Sheet dT*: AMINO MODIFIER-dT RESIDUE SUITABLE FOR FLUORESCEIN ISOTHIOCYANATE MODIFICATION.

B: BIOTINYLATED dT

X: INHIBITORY SUBSTITUTION, E.G. 1,4 ANHYDRO-D-RIBITOL.
Y: INHIBITORY SUBSTITUTION, E.G. CORDYCEPIN (3'DEOXYADENOSINE.)

ND INHIBITION

RELATED APPLICATIONS

This application is a division of Ser. No. 07/745,992 filed Aug. 16, 1991 U.S. Pat. No. 5,708,154, which is a continuation-in-part of Ser. No. 07/598,665 filed Oct. 23, 1990, which is a continuation-in-part of Ser. No. 07/317,670 filed Mar. 1, 1989, now abandoned, which is a continuation-in-part of Ser. No. 07/314,935 filed Feb. 24, 1989, now abandoned.

FIELD OF INVENTION

The copending related applications relate to heterologous block oligomers (HBO's). This invention relates to new classes of HBO's identified as modular nanostructure (MNS's) and to the use of MNS's in the detection and inhibition of retroviral reverse transcriptase. The invention also relates to radio-label free reverse transcriptase assays involving NS's, to the use of such assays to screen antiviral drugs and to novel reverse transcriptase inhibitors.

BACKGROUND OF THE INVENTION

The related parent applications describe inventions which utilize the capacity of nucleic acids for self assembly to construct a series of unimolecular DNA foldbacks or HBO's that are good enzyme substrates. In these molecules a long block of DNA is linked through a tether to a complementary short block of DNA. The tether may consist of dT residues, biotin residues, dodecyl phosphate residues, aminopropyl phosphate residues, or trivalent residues which are similar to the above but will allow for side-chain modification. These modifications may include chemiluminescent, fluorescent, or biotin moieties. The tether promotes intramolecular hybridization of the two regions of complementary DNA to form foldbacks having a free 3' hydroxyl on the short DNA strand and an overhanging DNA strand at the end of a short DNA-DNA hybrid. Appropriate HBO's have been shown to be substrates for restriction enzymes, human DNA methyl transferase and DNA polymerase I from *E. coli*.

Relevant to this invention is the discovery that DNA polymerase I is effective in extending each of the tethered foldbacks to a discrete length corresponding to full extension of the short block in the foldback using the 5' overhang as a template. Variation in the type of tether used permits chromatographic discrimination between otherwise isomeric forms of the molecules.

SUMMARY OF THE INVENTION

Somogyi, *Journal of Virological Methods*, 27:269–276 (1990) describes a solid phase reverse transcriptase microassay. Biotin is suggested as a replacement for tritium in the extant procedures. The invention provides modular nanostructures for use in the detection and inhibition of retroviral reverse transcriptase. For such purposes a relatively short block of DNA is linked to a longer block of RNA through a short tether of variable chemical composition. The tethered blocks are complementary to accommodate the formation of unimolecular foldbacks having a 3' hydroxyl on the DNA strand and an overhanging RNA strand at the end of a short DNA-RNA hybrid.

For reverse transcriptase detection, the tether will include labelled, preferably fluorescent moieties. Incubation of the foldback molecule with biotinylated nucleotide triphosphate precursors in the presence of reverse transcriptase yields a fluorescent product that can be concentrated by affinity binding to matrix bound avidin and detected by fluorescence.

For reverse transcriptase inhibition in living cells, the tether includes hydrophobic moieties to permit transport in liposomes and the penetration of cell membranes. The nanostructure for reverse transcriptase detection or inhibition may include appropriate substitutions. For example, to block enzyme activity, a stable abasic site analog may be included in the RNA strand or a cordycepin moiety may be present at the 3' end of the DNA strand.

DETAILED DESCRIPTION OF THE INVENTION

The expansion of the AIDS epidemic worldwide to between 10 and 30 million HIV positive individuals creates an urgent need for reliable and cost-effective HIV testing and for the screening of potential anti-viral drugs. The need is the greater due to other retroviral diseases such as hairy cell leukemia.

In one important embodiment, this invention provides a simply, highly sensitive, assay for HIV and other retroviral transcriptases which does not employ a radiolabel. This embodiment of the invention facilitates the direct screening of antiviral drugs by the rapid laboratory determination of viral titer in drug treated samples such as cell lines.

Another aspect of the invention permits evaluation of substrate specificity of HIV and other reverse transcriptases and so facilitates the design of deliverable inhibitors.

Figure 1:
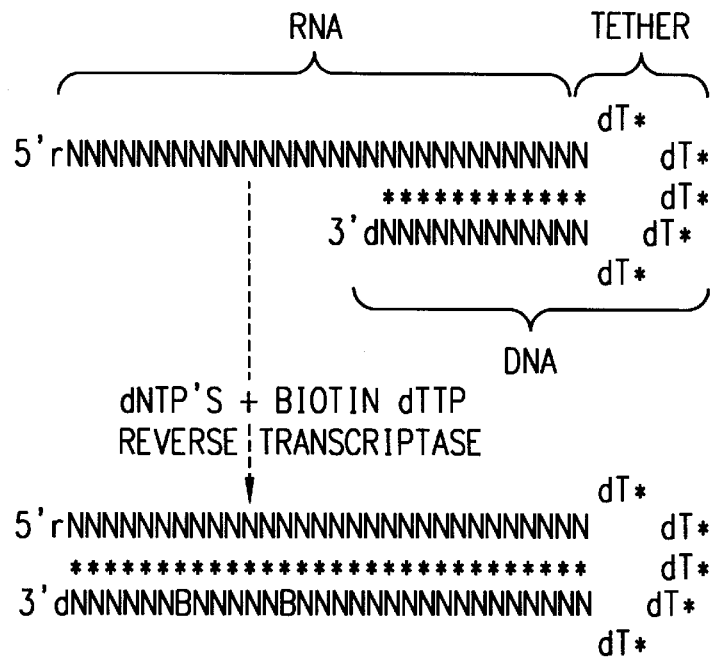
FIG. 1 illustrates the experimental design for the production of labelled biotinylated MNS's and the use thereof to detect reverse transcriptase activity.

FIG. 1 illustrates generally the synthesis of a RNA module 30 nucleotides in length from commercially available ribonucleotide precursors. As shown, five functionally modified "dT" moieties are then added to provide a fluorescent label in a tether module. The linked DNA module consists of 10 deoxynucleotides to provide Watson-Crick homology with the 3' end of the 30 mer and thus form the folded substrate molecule (MNS) shown in FIG. 1.

Incubation of this substrate molecule with active reverse transcriptase in the presence of biotinylated deoxynucleotide precursors yields the biotinylated product shown in FIG. 1.

The extent of recovery of the fluorescent product with an avidin based matrix, e.g., in a streptavidin agarose minicolumn, is a function of the activity of reverse transcriptase.

The fluorescent product is quantitated by fluorimetry.

Advantages of this procedure for detecting and quantitating reverse transcriptase are (1) radioactive compounds are not required; (2) sensitivity can be increased by increasing sample size and concentrating the product; and (3) the sequence of the substrate MNS's and its composition—i.e., RNA-DNA; RNA-RNA, can be chosen to optimize the observed activity or increase its specificity for a given species of reverse transcriptase.

A practical application of this aspect of the invention is an assay to detect or quantify reverse transcriptase in physiological samples. The assay entails procurement of a sample from a patient suspected of viral infection, e.g., a patient who may be HIV positive, incubating the sample in the presence of a biotinylated triphosphate with a MNS having a fluorescent tether, recovering the biotinylated product, if any, on an avidin matrix, and quantifying the biotinylated product if present.

The invention includes kits comprising an appropriate fluorescent labelled MNS, and biotinylated dioxynucleotide triphosphate precursor.

EXAMPLE I

Synthesis and Use of a Simple Reverse Transcriptase Substrate

The sequence of each of the three modules in the HBO can be chosen by the investigator. Sequences identical to those of the HIV, and HTLV-I initiation site may be especially useful. In order to provide clarity in this example a simple sequence is used to illustrate the method.

HBO Synthesis

Synthesis of the HBO begins with the 3' matrix-bound phosphoramidite precursor of Thymidine (dT). Programmed DNA synthesis is continued using standard methods in an ABI DNA synthesizer until 12 residues of dT have been added. This constitutes the complementary DNA module. The loop module is synthesized beginning with the addition of two dC residues, after which the system reaches a preprogrammed stop. At this point the investigator manually carries out one cycle of DNA synthesis in which a trifunctional dT residue carrying a masked primary amine is added to the growing chain. Two additional dC residues are added to the growing chain to complete the loop module. The RNA module in the HBO is begun by the addition of 30 Adenine (A) residues using protected riboprecursors and standard RNA synthesis methods. Once the HBO is completed, it is cleaved from the matrix and the masked amino group on the trifunctional dT residue in the loop module is reacted with fluorescein isothiocyanate (FTIC).

Based on our previous work with partially complementary molecules of this type, the HBO will self-associate to form the modular nanostructure depicted below.

5'AAAAAAAAAAAAAAAAAAAAAAAAAAAAAA
    CC
    *********** dT-FITC
3'TTTTTTTTTTTT CC

Based on our experience with DNA polymerases, this nanostructure is expected to be a self-priming substrated for reverse transcriptase.

Reverse Transcriptase Assay

A standard reaction mixture containing: 50 mM Tris-HCl (pH 8.3), 40 mM KCl, 6 mM $MgCl_2$, 1 mM Dithiothreitol, 0.1 mg/ml RNAse free Bovine Serum Albumin and 0.1 mM HBO substrate is then incubated with a reverse transcriptase preparation in 50 µl total volume for 10 minutes at 37° C. in the presence of 0.5 mM Biotinylated dTTP.

HBO's that have been extended by reverse transcriptase will now contain at least 1 biotinylated dT residue, and will therefore be retained by commercially available streptavidin-Agarose. The reverse transcriptase product will be isolated by passage of the complete reaction mixture through a 50 µl column of commercially available streptavidin agarose. After washing with 1 ml of Tris-HCl (pH 8.3), 400 mM KCl, the amount of fluorescein-containing substrate retained by the agarose can be quantified by fluorimetry on the suspended agarose slurry. Alternatively the fluorescein-containing substrate can be eluted from the agarose with a solution containing a strong denaturant, like 6 M guanidine HCl at pH 1.5, and fluorometric quantification of the fluroescein-containing substrate can be carried out in a neutralized solution.

Figure 2:
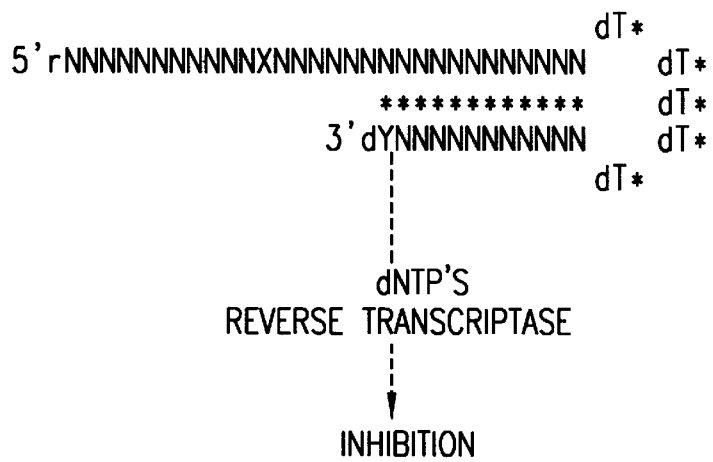
FIG. 2 illustrates the experimental design for development of a family of reverse transcriptase inhibitors based, in part, on substitution in the modular nanostructure.

FIG. 2 illustrates procedures for preparing one or more reverse transcriptase inhibitors based on substitutions in the nanostructure. A MNS similar to that shown n FIG. 1 is utilized with the exception that the amino modifier dT used in the tether is a hydropholic moiety, i.e., dodecylphosphate to facilitate liposome transport, and an enzyme inhibitory substitution, e.g., 1,4-Anhydro-D-Ribitol is present in the RNA template of the nanostructure. An enzyme inhibitory moiety, e.g., cordycepin (3' deoxyAdenosine) may alternatively or additionally be included at the 3' end of the DNA strand.

Inhibition of HIV reverse transcriptase is accomplished by incorporation of the MNS's into liposomes for transport to and penetration of cell membranes.

EXAMPLE II

Synthesis of a Simple Reverse Transcriptase Inhibitor

As with the HBO described in Example I, a simple sequence is used to illustrate the preparation of an inhibitory substrate.

HBO Synthesis

Synthesis of the HBO begins with the 3' matrix-bound phosphoramidite precursor of Thymidine (dT). Programmed DNA synthesis is continued using standard methods in an IBI DNA synthesizer until 12 residues of dT have been added. This constitutes the complementary DNA module. The loop module is then synthesized by adding 5 dC residues to the growing chain using standard methods. The RNA module in the HBO is begun by the addition of 15 Adenine (A) residues using protected riboprecursors and standard RNA synthesis methods, after which the system reaches a preprogrammed stop. The investigator then performs one cycle of manual DNA synthesis to introduce a 1,4-Anhydro-D-Ribitol (x) phosphoramidite into the growing RNA module. The RNA module is then completed by the automated addition of 14 additional Adenine (A) residues.

Based on our previous work with partially complementary molecules of this type, the HBO will self-associate to form the modular nanostructure depicted below.

5' AAAAAAAAAAAAAAxAAAAAAAAAAAAAA
CC
************ C
3' TTTTTTTTTTTT CC

As noted above, the nanostructure is expected to be a self-priming substrate for reverse transcriptase. Analogous DNA substrates inhibit DNA polymerases because the abasic site analog does not provide a mechanism for base-pair formation with an incoming nucleoside triphosphate precursor. Thus the nanostructure depicted above is expected to permit initiation but block elongation by reverse transcriptase after the addition of three nucleotides to the DNA module. Thus its net effect is to inhibit the enzyme.

We claim:

1. An assay for determining the presence of absence of reverse transcriptase in a physiological sample which comprises (i) contacting said sample in the presence of a biotinylated deoxynucleotide triphosphate precursor with a modular nanostructure, said nanostructure comprising:

a relatively long RNA sequence and a relatively short RNS sequence, the 3' terminal nucleotide of the relatively long RNA sequence being covalently linked by a fluorescent tether to the 5' terminal nucleotide of the relatively short RNA sequence, said relatively long and relatively short RNA sequences being complementary in portions of said sequences adjacent said tether and functioning respectively as a template and a primer in the presence of reverse transcriptase;

(ii) recovering the fluorescent biotinylated product, if any, on an avidin based matrix;

(iii) eluting said product from said matrix;

(iv) detecting said product in said eluate; or (v) detecting said product while bound to the matrix.

2. An assay as defined in claim 1 further comprising quantifying said product in said eluate by fluorimetry.

* * * * *